United States Patent
Macy (10) Patent No.: US 10,406,321 B1
(45) Date of Patent: Sep. 10, 2019

(54) METHOD AND APPARATUS FOR INSERTION OF A CATHETER WITH A PROXIMAL CONNECTOR WHILE MONITORING BLOOD PRESSURE

(71) Applicant: Johnathan Ivan Macy, Virginia Beach, VA (US)

(72) Inventor: Johnathan Ivan Macy, Virginia Beach, VA (US)

( * ) Notice: Subject to any disclaimer, the term of this patent is extended or adjusted under 35 U.S.C. 154(b) by 453 days.

(21) Appl. No.: 13/694,797

(22) Filed: Jan. 7, 2013

(51) Int. Cl.
*A61M 5/178* (2006.01)
*A61M 25/01* (2006.01)
*A61M 25/09* (2006.01)

(52) U.S. Cl.
CPC ...... *A61M 25/01* (2013.01); *A61M 25/09041* (2013.01)

(58) Field of Classification Search
CPC .......... A61M 25/0017; A61M 25/0111; A61M 25/0113; A61M 25/09041; A61B 1/018
See application file for complete search history.

(56) References Cited

U.S. PATENT DOCUMENTS

| | | | |
|---|---|---|---|
| 3,774,605 A | | 11/1973 | Jewett |
| 3,835,854 A | * | 9/1974 | Jewett ................ A61M 25/0113 604/159 |
| 3,838,688 A | | 10/1974 | May |
| 4,326,520 A | | 4/1982 | Alley |
| 5,048,537 A | * | 9/1991 | Messinger ........... A61B 5/0215 600/486 |
| 5,389,100 A | * | 2/1995 | Bacich ............... A61M 25/0119 604/159 |
| 2004/0111138 A1 | * | 6/2004 | Bleam ....................... A61F 7/12 607/105 |
| 2007/0225687 A1 | * | 9/2007 | House ................ A61M 25/0111 604/544 |

FOREIGN PATENT DOCUMENTS

WO   WO 2012011762   * 12/2012

OTHER PUBLICATIONS

U.S. Appl. No. 13/507,984, filed Aug. 10, 2012, Macy.
Centers for Disease Control, Guidelines for the Prevention of Intravascular Catheter-Related Infection, 2011.

* cited by examiner

*Primary Examiner* — Matthew F Desanto (57) ABSTRACT

A method and apparatus for inserting a conventional flexible catheter with a pre-attached connector on the proximal end into a vessel, such as a vein or artery in a cardiovascular system, while monitoring blood pressure. The catheter drive assembly has an external drive input for advancement and retraction of the flexible catheter. The catheter drive assembly has cylindrical catheter drives that can be engaged to or disengaged from the flexible catheter without causing damage to the flexible catheter. The flexible catheter distal end provides fluid communication to a disposable blood pressure transducer. The flexible catheter is completely encapsulated within a protective sleeve and within the catheter drive assembly, creating an aseptic insertion environment, eliminating the need for sterile barrier protection. Once the flexible catheter is inserted to the desired position, the protective sleeve and catheter drive assembly are removed from the flexible catheter leaving the flexible catheter.

14 Claims, 9 Drawing Sheets

METHOD AND APPARATUS FOR INSERTION OF A CATHETER WITH A PROXIMAL CONNECTOR WHILE MONITORING BLOOD PRESSURE

TECHNICAL FIELD

The present invention relates to methods and devices designed for manipulating a flexible catheter, as during the feeding of the flexible catheter into a vein or artery of a patient. In particular, an apparatus and method to facilitate a simple, closed system, controlled insertion of a flexible catheter while enabling the blood pressure to be monitored through the internal lumen of the flexible catheter. The invention enables the use of a catheter with a pre-attached connector and with or without a wire or stylet.

BACKGROUND OF PRIOR ART

This is a continuation of application Ser. No. 13/507,984 filed Aug. 10, 2012.

The following are some prior art that presently appears relevant:

U.S. Patents

| Pat. No. | Issue Date | Patentee |
| --- | --- | --- |
| 4,326,520 | Apr. 27, 1982 | Alley |
| 3,774,605 | Nov. 27, 1973 | Jewett |
| 3,838,688 | Oct. 1, 1974 | May, Wilks |

NON PATENT LITERATURE DOCUMENTS

Department of Health and Human Services, Centers for Disease Control, "Guidelines for the Prevention of Intravascular Catheter-Related Infection" (2011)

New Technologies to Prevent Intravascular Catheter-Related Bloodstream Infections. Emerg Infect Dis [serial on the Internet]. 2001 March-April [date] http://wwwnc.cdc.gov/eid/article/7/2/70-0197.htm In current medical practice, it is often necessary to have access to the venous system of a patient. To obtain access to the venous system a tube (a "flexible catheter") can be inserted into a vein of the patient. Flexible catheters that are used today come in a range of configurations including single or multi lumen and with or without a wire or stylet. Many times a catheter will include a wire or stylet in the inside lumen to add rigidity to the flexible catheter for insertion. Additionally, flexible catheters that are used today have a pre-attached standard connector on the proximal end for each lumen of the catheter. Using the catheter, it is a common procedure to obtain diagnostic information about the heart such as the central venous pressure. Often catheterization is necessary to deliver fluids, such as medications, into the patient's venous system. Additionally, it may be necessary to aspirate fluids from the catheter site to evaluate blood profiles, perform diagnostic assays, etc.

Typically, catheterization starts by measuring the length from the desired placement of the distal end of the catheter to the planned insertion site. The insertion site on the skin of the patient is prepped by cleaning and the use of an antimicrobial solution. In the Centers for Disease Control's (CDC) publication, Guidelines For The Prevention of Intravascular Catheter-Related Infection, 2011, the CDC recommends the use of maximal sterile barrier precautions for catheter insertion. Maximal sterile barrier precautions include the use of cap, mask, sterile gown, sterile gloves and a sterile full body drape on the patient. These maximal sterile barrier precautions apply to both central venous catheters and peripheral inserted central catheters that are inserted in an open environment setting. Open environment insertion is defined as the exterior surface of the catheter being exposed to the surrounding environment. Maximal sterile barrier precautions are done in an attempt to minimize the risk of catheter-related bloodstream infections.

The physician implants a device called an introducer sheath into the patient's vein using standard procedural techniques. A flexible catheter is threaded through the introducer sheath into the patient's vein. The catheter is inserted until the desired insertion length is achieved. If the flexible catheter had a wire or stylet it is removed after the insertion length is achieved. The introducer sheath is removed from the patient and separated into halves from the flexible catheter. The placement location of the distal end of the catheter is then verified using Ultra Sound or X-ray. The preferred method is to use X-ray since it is difficult to see behind breast bones using Ultra Sound. Typical procedure time for the insertion of a flexible catheter ranges from 30 to 45 minutes.

As stated by Alley, U.S. Pat. No. 4,326,520, during catheter insertion there is a need to have controlled, alternating insertion and retraction threading of the catheter within the blood vessel. The manipulation of the catheter is necessary because it may get stuck due to obstructions. During insertion, a catheter can also turn and go into a non desired part of the vascular system. For example, frequently a catheter introduced through a forearm vein (brachial vein) intended to lie in the superior vena cava to measure central venous pressure will enter the internal jugular vein and be directed toward cerebral circulation. The need to verify placement of the distal end of the catheter using Ultra Sound or X-ray is because the catheter can go into a non desired part of the vascular system.

A publication on the CDC web site states that approximately 80,000 catheter-related bloodstream infections occur in U.S. intensive-care units each year. The annual cost from these infections is estimated to be between $296 million and $2.3 billion. These infections are associated with 2,400 to 20,000 deaths per year.

Several types of closed systems to address the infection problem have been proposed for catheter insertion—for example U.S. Pat. No. 4,326,520 (1982) to Alley, U.S. Pat. No. 3,744,605 (1973) to Jewett and U.S. Pat. No. 3,838,688 (1974) to May and Wilks. The proposed closed systems do not mention or incorporate the capability of measuring blood pressure during catheter insertion and manipulation. The proposed closed systems do not mention the use of a catheter with multi lumens or a catheter with a wire or stylet.

All catheter insertion methods heretofore known suffer from a number of disadvantages.

(a) Catheters that have an increased risk of infection require the use of maximal sterile barrier precautions.
(b) Catheters requiring maximal sterile barrier precautions are not easily used in an emergency or combat situation.
(c) Catheters requiring a 30 to 45 minute procedure are not suitable for an emergency or combat situation.
(d) Availability to the necessary Ultra Sound or X-Ray equipment for catheter distal end verification can be limited and time consuming.
(e) Completely closed systems prohibit the monitoring of blood pressure during insertion.

(f) Systems that place continuous pressure on the catheter during sterilization and storage prior to use cause the catheter to become deformed at the point of contact.
(g) Proposed closed systems do not enable the use of a multi lumen catheter or a catheter with a wire or stylet.

SUMMARY

This invention relates to a flexible catheter insertion apparatus used in the cardiovascular systems of humans and animals. In the applicant's co-pending application, application Ser. No. 13/507,984, Aug. 10, 2012, an insertion apparatus is described which includes a catheter drive assembly, a pressure line, a disposable blood pressure transducer, a flexible catheter, an introducer sheath and an intravenous solution source. The catheter drive assembly includes an external drive and an external means to engage or disengage the catheter drive assembly onto the surface of the flexible catheter. The external drive provides precise control of movement for the flexible catheter distal end during insertion or retraction. The device of the co-pending application, as well as the device of the present invention, maintain the catheter in a sterile condition prior to and while it is being inserted.

The present invention generally provides the benefits and advantages of the co-pending application but has a number of significant improvements. For example, the device disclosed in the co-pending application had the flexible catheter passing through the catheter drive assembly. Consequently, the flexible catheter had to have a connector attached after insertion. The new design allows a catheter with a pre-attached connector on the proximal end to be utilized. The new design also enables the use of a multi lumen catheter and a catheter with a wire or stylet. The greater flexibility to use various styles of catheters enables the new design to meet a broader range of clinical needs.

An introducer sheath is inserted into a patient's vein using acceptable clinical practice. The catheter is primed with a suitable intravenous solution to expel all the air from the catheter. The disposable blood pressure transducer proximal end is connected to a suitable intravenous solution source. The flexible catheter distal end is inserted into the introducer sheath proximal end. The catheter drive assembly distal connector is connected to the introducer sheath proximal connector. The catheter drive assembly is engaged using the external engagement selector actuator. With the disposable blood pressure transducer connected to a blood pressure monitor the flexible catheter is advanced into the patient to the desired location. In alternative applications where the reading of the blood pressure is not desired, the catheter is individually inserted. Various combinations of catheters can be inserted in an aseptic manner. These combinations include, single lumen, multi lumen, with wire or stylet, without wire or stylet, monitoring blood pressure or not monitoring blood pressure. It should be noted that a single lumen catheter with a wire or stylet cannot monitor blood pressure during insertion.

The catheter drive assembly, when engaged, places sufficient pressure on the flexible catheter to propel the flexible catheter to achieve insertion or retraction. The catheter drive assembly, when engaged, does not occlude the flexible catheter's interior lumen. The flexible catheter's interior lumen cross sectional area is sufficient to communicate pressure signals from the flexible catheter distal end to the disposable blood pressure transducer. When the flexible catheter distal end is in the superior vena cava a central venous pressure waveform will be displayed on the blood pressure monitor. A combination of the flexible catheter insertion length and the central venous pressure waveform confirms the placement of the flexible catheter distal end thereby eliminating the need for verification thru the use of Ultra Sound or X-ray.

The flexible catheter is encapsulated within the protective sleeve and the catheter drive assembly thus eliminating the need for maximal sterile barrier precautions. The current time needed for catheter insertion requiring maximal sterile barrier precautions is 30 to 45 minutes. By eliminating the need for maximal sterile barrier precautions, the apparatus can insert the flexible catheter in a matter of minutes compared to current standards. The reduction in time and elimination of the sterile barrier precautions allows the apparatus to be used in emergency and combat settings.

The catheter drive assembly is placed in the disengaged position after manufacture. With the catheter drive assembly disengaged no pressure or force is applied to the flexible catheter. This ensures that the flexible catheter will not be deformed from sterilization or storage prior to use. After the flexible catheter is inserted, the protective sleeve and catheter drive assembly is removed and disposed of thereby leaving the flexible catheter remaining.

DRAWINGS—REFERENCE NUMERALS 20 catheter drive assembly
21 housing
22 housing distal connector
23 housing proximal connector
24 housing seal surface
25 movable drive bottom
26 movable cylindrical catheter drive
27 movable drive top
28 fixed cylindrical catheter drive
29 internal sealing cap
31 movable drive rotating arm
32 external engagement actuator
34 fixed drive gear
35 main drive gear
36 external drive
37 bottom cover
38 housing finger flange
39 removable cover
40 cover pullout tab
41 end shield
50 flexible catheter
51 flexible catheter distal end
52 flexible catheter proximal end with connector
60 pressure line
61 pressure line distal connector
62 pressure tubing
63 pressure line proximal connector
70 disposable blood pressure transducer
71 disposable blood pressure transducer distal connector
72 disposable blood pressure transducer proximal connector
73 disposable blood pressure transducer wire lead
74 disposable blood pressure transducer plug connector
80 introducer sheath
81 introducer sheath proximal connector
82 introducer sheath tubular member
90 protective sleeve assembly
91 protective sleeve
92 protective sleeve collar
93 sleeve pull tab
94 weakened portions
100 catheter insertion assembly

DESCRIPTION OF THE EMBODIMENTS

Figure 1:
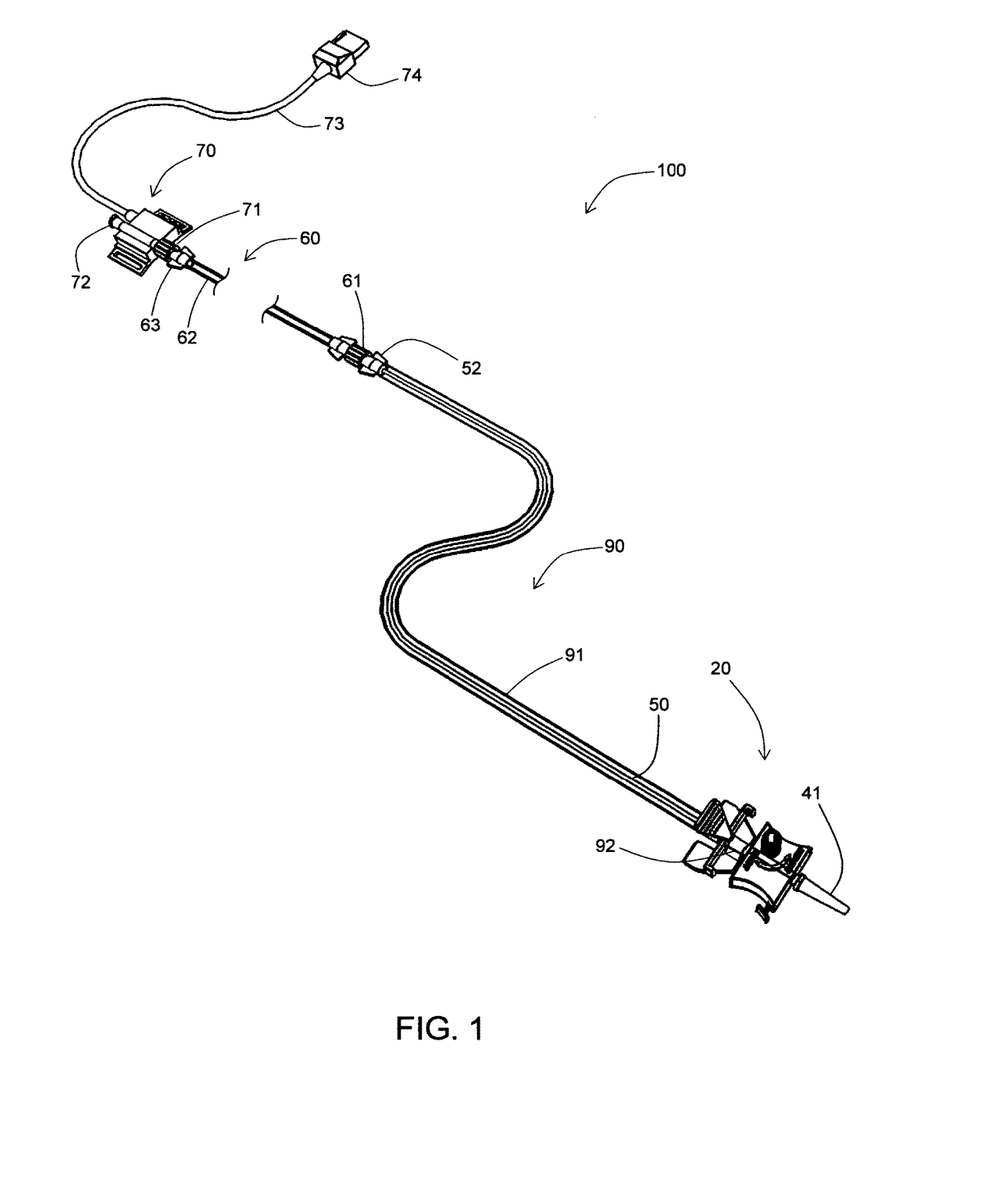
FIG. 1 is a perspective view of the catheter insertion assembly comprised of a disposable blood pressure transducer, a pressure line, a protective sleeve assembly, a catheter drive assembly, a single lumen flexible catheter with a pre-attached proximal connector and an end shield.
Figure 4:
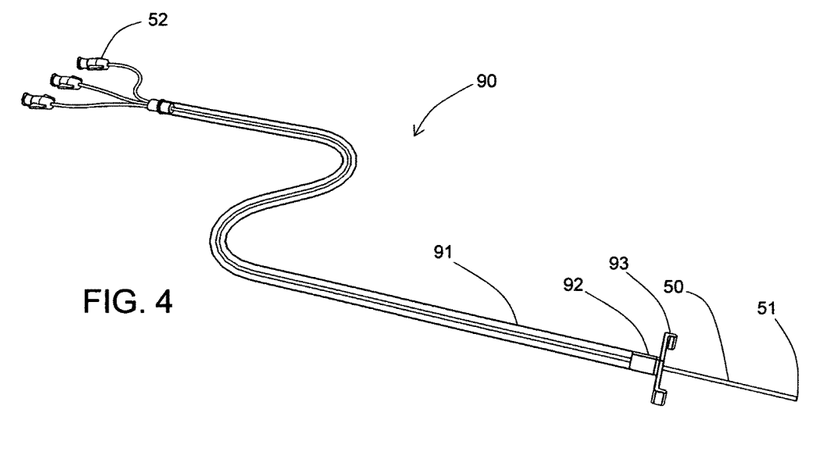
FIG. 4 is a perspective view of the protective sleeve assembly encapsulating a multi lumen flexible catheter.

Referring to FIG. 1, the catheter insertion assembly 100 is comprises a catheter drive assembly 20, a flexible catheter 50, a pressure line 60, a disposable blood pressure transducer 70 and a protective sleeve assembly 90. The pressure line 60 comprises a pressure line distal connector 61, a pressure tubing 62 and a pressure line proximal connector 63. The disposable blood pressure transducer 70 is comprises a disposable blood pressure transducer distal connector 71, a disposable blood pressure transducer proximal connector 72, a disposable blood transducer pressure wire lead 73 and a disposable blood pressure transducer plug connector 74. The disposable blood pressure transducer 70 is commercially available and is manufactured in compliance with FDA requirements. The protective sleeve assembly 90 comprises a protective sleeve 91 and a protective sleeve collar 92 as shown in FIG. 4. The catheter drive assembly 20 comprises a housing 21, a catheter drive mechanism comprising a movable drive bottom 25, a movable cylindrical catheter drive 26, a fixed cylindrical catheter drive 28, a fixed drive gear 34, a main drive gear 35, and a movable drive top 27; an internal sealing cap 29; a movable drive rotating arm 31; an external engagement actuator 32; an external drive 36; a bottom cover 37; a removable cover 39 and an end shield 41. Each item associated with the catheter drive assembly 20 will be described and explained in subsequent figures. The flexible catheter distal end 51 is covered by the end shield 41. Each item associated with catheter drive assembly is described and explained in subsequent figures. The flexible catheter distal end 51 is covered by the end shield 41. The flexible catheter 50 extends through the catheter drive assembly 20 and into the protective sleeve assembly 90. The flexible catheter proximal end with connector 52 is attached to the pressure line distal connector 61. The pressure line proximal connector 63 is attached to the disposable blood pressure transducer distal connector 71. The flexible catheter 50 is completely encapsulated by the catheter drive assembly 20 and the protective sleeve assembly 90.

Figure 2:
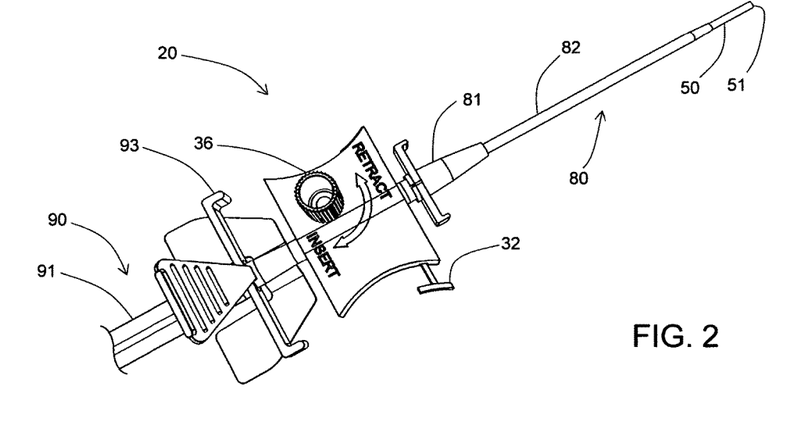
FIG. 2 is a perspective view illustrating the apparatus connected to an introducer sheath.

FIG. 2 shows an introducer sheath 80 comprised of an introducer sheath proximal connector 81 and an introducer sheath tubular member 82. The catheter drive assembly 20 is connected to the introducer sheath proximal connector 81. The illustration does not show the introducer sheath 80 inside a vessel but that can be implied as a common use of the introducer sheath to deliver flexible catheter 50 into the vessel to which access has been achieved. Provided that the introducer sheath 80 has achieved vessel access, the apparatus, with the external engagement actuator 32 engaged and by turning the external drive 36, the flexible catheter distal end 51 will be advanced into the vessel. The flexible catheter 50 and flexible catheter distal end 51 have an outside diameter that is smaller than the introducer sheath 80 inside diameter. Also shown is the distal end of the protective sleeve assembly 90 engaged with the catheter drive assembly 20. Two sleeve pull tabs 93 are shown extending outward. The two sleeve pull tabs 93 are used to remove the protective sleeve assembly 90 from the flexible catheter 50.

Figure 3:
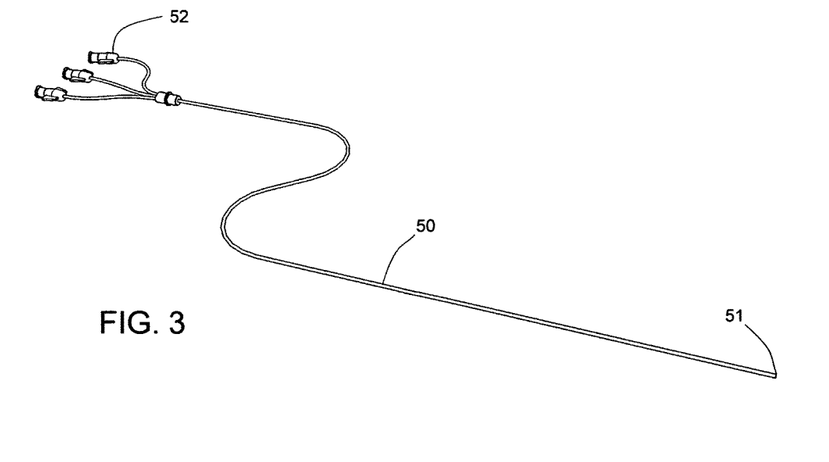
FIG. 3 is a perspective view illustrating a multi lumen flexible catheter with proximal end pre-attached connectors and a distal end.

FIG. 3 shows a multi lumen flexible catheter 50 with the flexible catheter distal end 51 and the flexible catheter proximal end with connector(s) 52. The flexible catheter distal end 51 and the flexible catheter 50 have a consistent outside diameter. Typically, one flexible catheter proximal end with connector 52 is pre-attached for each individual lumen in the flexible catheter 50. If the flexible catheter 50 has one lumen then there is one flexible catheter proximal end with connector 52. If the flexible catheter 50 has three lumens then there are three flexible catheter proximal end with connector(s) 52 as shown in FIG. 3.

Figure 8:
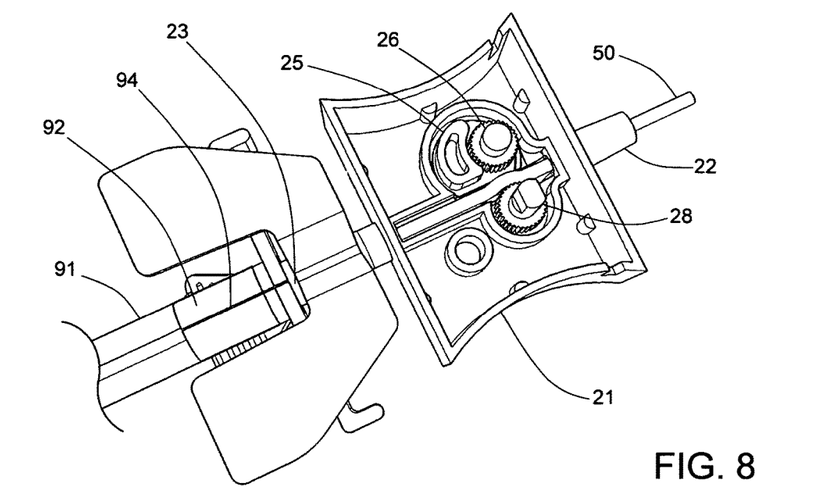
FIG. 8 is a perspective view of the housing from the bottom showing the cylindrical catheter drives disengaged and the flexible catheter.

FIG. 4 shows the orientation of the flexible catheter 50 and flexible catheter distal end 51 to the protective sleeve assembly 90. The length of flexible catheter 50 is fully encapsulated in the protective sleeve assembly 90. The protective sleeve assembly 90 has a protective sleeve 91 that is attached to the protective sleeve collar 92. The protective sleeve collar 92 has two sleeve pull tabs 93 that extend outward and that are suitable to be grasped with fingers. The protective sleeve collar 92 has two weakened portions 94 as illustrated in FIG. 8. When a force is applied to the two sleeve pull tabs 93, in a direction perpendicular to the axis of the protective sleeve collar 92, the two weakened portions 94 fail allowing the protective sleeve collar 92 to separate into two halves. With the protective sleeve 91 attached to the protective sleeve collar 92, separating the protective sleeve collar 92 causes the protective sleeve 91 to separate. Further pulling the protective sleeve collar 92 apart causes the protective sleeve 91 to continue to separate thereby removing the protective sleeve assembly 90 from the flexible catheter 50. The protective sleeve collar 92 would be made of acceptable medical grade plastic that can be precision injection molded. The protective sleeve 91 would be made of acceptable clear medical grade plastic that can be extruded and has the material characteristics that would allow for linear tearing. The material used for the protective sleeve 91 would be thin in nature and flexible. The protective sleeve 91 can be attached to the protective sleeve collar 92 using ultra sonic or heat bonding. The flexible catheter 50 is preferably constructed from a bio-compatible thermoplastic material that can be extruded. The flexible catheter proximal end with connector 52 would be made of acceptable medical grade plastic that can be precision injection molded. The flexible catheter 50 is attached to the flexible catheter proximal end with connector 52 using solvent bonding.

Figure 5:
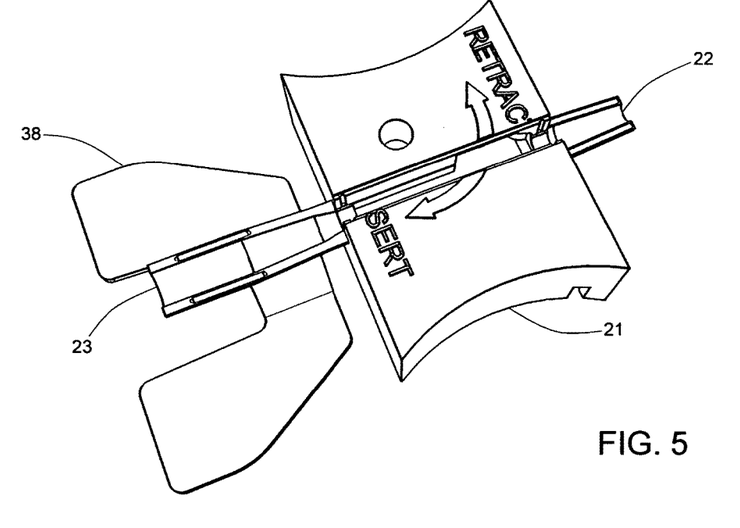
FIG. 5 is a perspective view of the housing from the top.

FIG. 5 shows a perspective top view of a housing 21. The perspective top view of housing 21 shows an opening the length of the housing 21 across the top. The opening that is the length of the housing 21 is of sufficient size to allow the flexible catheter 50 to be easily removed. The housing 21 incorporates a housing finger flange 38. The housing 21 incorporates the bottom half of the housing distal connector 22 and the housing proximal connector 23.

Figure 6:
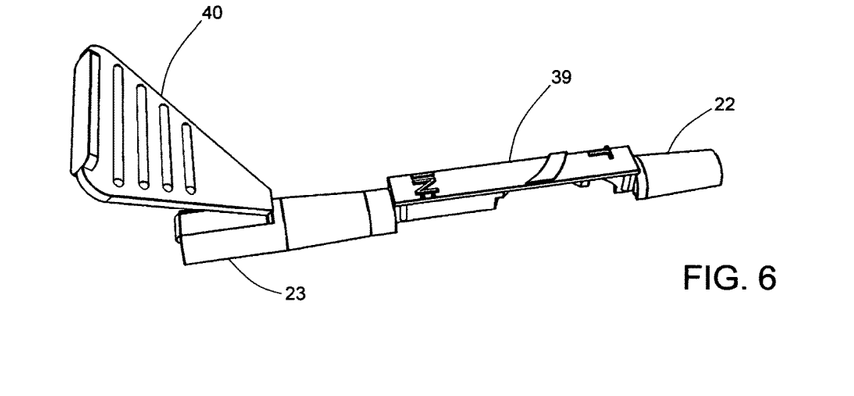
FIG. 6 is a perspective view of the removable cover and the cover pullout tab.

FIG. 6 shows a perspective top view of a removable cover 39. The removable cover 39 incorporates a cover pullout tab 40. The removable cover 39 incorporates the top half of the housing distal connector 22 and the housing proximal connector 23. Part of the cover pullout tab 40 is recessed into the top half of the housing proximal connector 23 providing clearance for the protective sleeve collar 92. The removable cover 39 is inserted into the housing 21 from the top.

Figure 7:
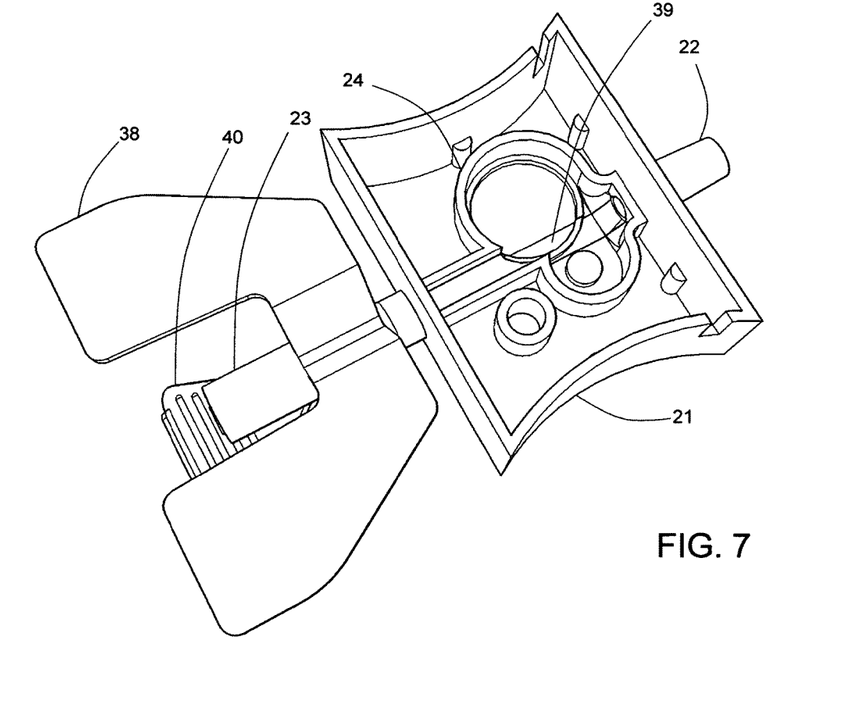
FIG. 7 is a perspective view of the housing from the bottom showing the removable cover inserted into the housing from the top.

FIG. 7 shows a perspective bottom view of the housing 21. The removable cover 39 is shown to be inserted in the housing 21. The housing 21 incorporates the bottom half of the housing distal connector 22 and the housing proximal connector 23. The removable cover 39 incorporates the top half of the housing distal connector 22 and the housing proximal connector 23. When the removable cover 39 is inserted into the housing 21 the housing distal connector 22 and the housing proximal connector 23 are formed. The housing 21 incorporates a housing seal surface 24 that is used to seal to the internal sealing cap 29 shown in FIG. 12. The design of the housing 21 and the removable cover 39 is sufficient such that the interfacing surfaces of the housing 21 and the removable cover 39 create a seal.

FIG. 8 shows a perspective bottom view of the housing 21 with a movable bottom drive 25, a movable cylindrical catheter drive 26, a fixed cylindrical catheter drive 28 and a flexible catheter 50. The movable bottom drive 25 is located in the housing 21 using a cylindrical pocket to provide orientation. The movable drive bottom 25 rotates around the axis of the movable drive bottom 25. The movable cylindrical catheter drive 26 fits onto the movable drive bottom 25. The axis of the movable cylindrical catheter drive 26 is offset from the movable drive bottom 25 axis. When the movable drive bottom 25 is rotated, the spacing can be increased or decreased between the moveable cylindrical catheter drive 26 and the fixed cylindrical catheter drive 28. The movable drive bottom 25 and the movable cylindrical catheter drive 26 are shown in the disengaged position. In the disengaged position, no pressure is placed on the flexible catheter 50 by the movable cylindrical catheter drive 26 or the fixed cylindrical catheter drive 28. The disengaged space between the surface of the movable cylindrical catheter drive 26 and the surface of the fixed cylindrical catheter drive 28 is greater than the flexible catheter 50 outside diameter. The catheter drive assembly 20 in the disengaged position allows the catheter insertion assembly 100 to be sterilized and stored prior to use without causing deformation to the flexible catheter 50. The following features are described in the co-pending application and form no part of the present invention. The protective sleeve collar 92, with the protective sleeve 91 attached, is shown connected over the housing proximal connector 23. The protective sleeve collar 92 has two weakened portions 94. The two weakened portions 94 are located 180 degrees apart along the protective sleeve collar 92. The two weakened portions 94 extend the full axial length on the protective sleeve collar 92. The flexible catheter 50 is shown extending from the protective sleeve 91 through the housing 21 and out the housing distal connector 22.

Figure 9:
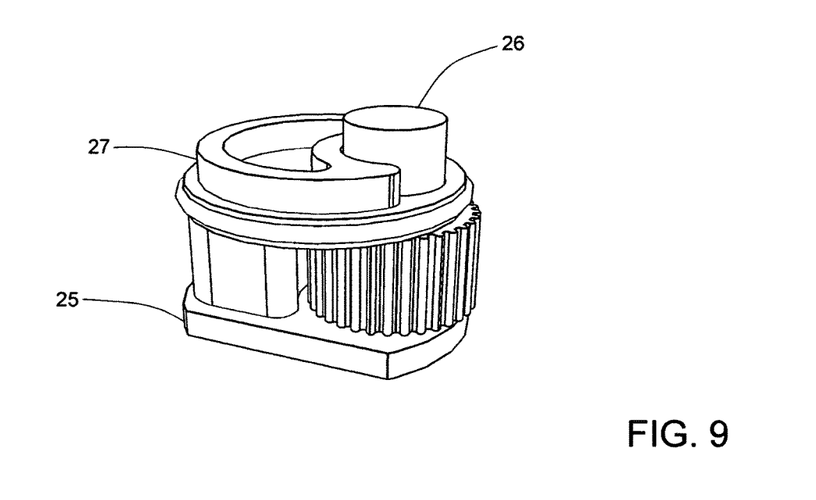
FIG. 9 is a perspective view of the moveable cylindrical catheter drive assembled to a movable drive top and a moveable drive bottom.

FIG. 9 shows the movable drive bottom 25, the movable cylindrical catheter drive 26 and the movable drive top 27 in the assembled location. The movable drive bottom 25 and the movable drive top 27 rotate around the same axis. The movable cylindrical catheter drive 26 shaft extends up through the movable drive top 27. The movable cylindrical catheter drive 26 shaft and the movable drive top 27 interface is of sufficient design to create a rotating seal. The movable drive bottom 25 has a section removed to provide clearance for the flexible catheter 50 to be removed from the top of the catheter drive assembly 20 when the catheter drive assembly 20 is in the disengaged position.

Figure 10:
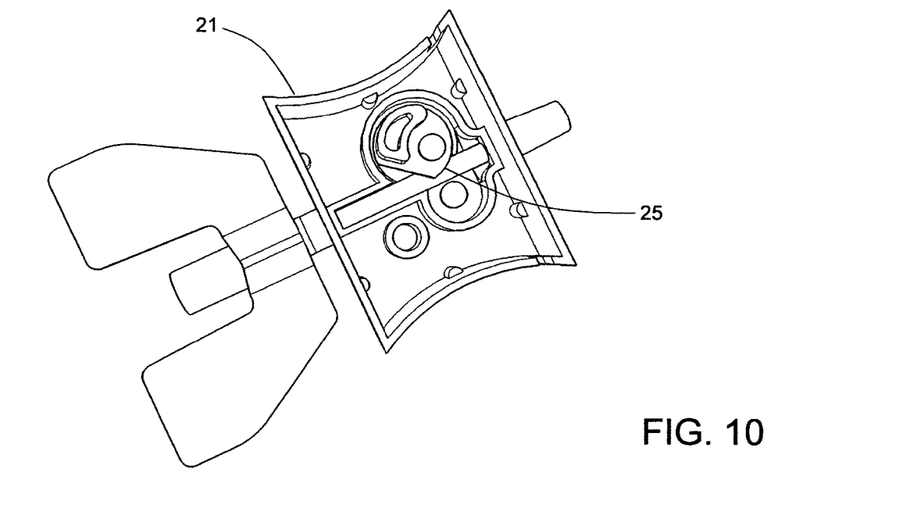
FIG. 10 is a perspective view of the housing from the bottom with the moveable drive bottom in the engaged position.

FIG. 10 shows a perspective view from the bottom of the housing 21 with the movable drive bottom 25. The movable drive bottom 25 is shown in the engaged position. With the movable drive bottom 25 in the engaged position, a portion of the movable drive bottom 25 extends over the top opening of housing 21. With the catheter drive assembly 20 in the engaged position, the flexible drive catheter 50 cannot be removed with the movable drive bottom 25 blocking the opening.

Figure 11:
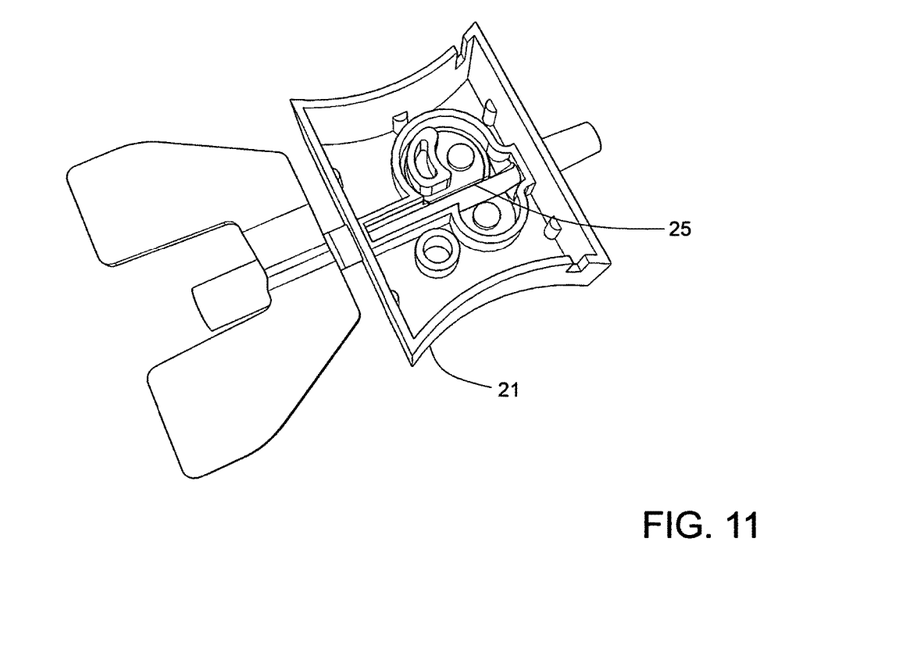
FIG. 11 is a perspective view of the housing from the bottom with the moveable drive bottom in the disengaged position.

FIG. 11 shows a perspective view from the bottom of the housing 21 with the movable drive bottom 25. The movable drive bottom 25 is shown in the disengaged position. With the movable drive bottom 25 in the disengaged position, the movable drive bottom 25 does not interfere with the opening in the top of housing 21. With the movable drive bottom 25 in the disengaged position, the flexible catheter 50 can be removed from the catheter drive assembly 20.

Figure 12:
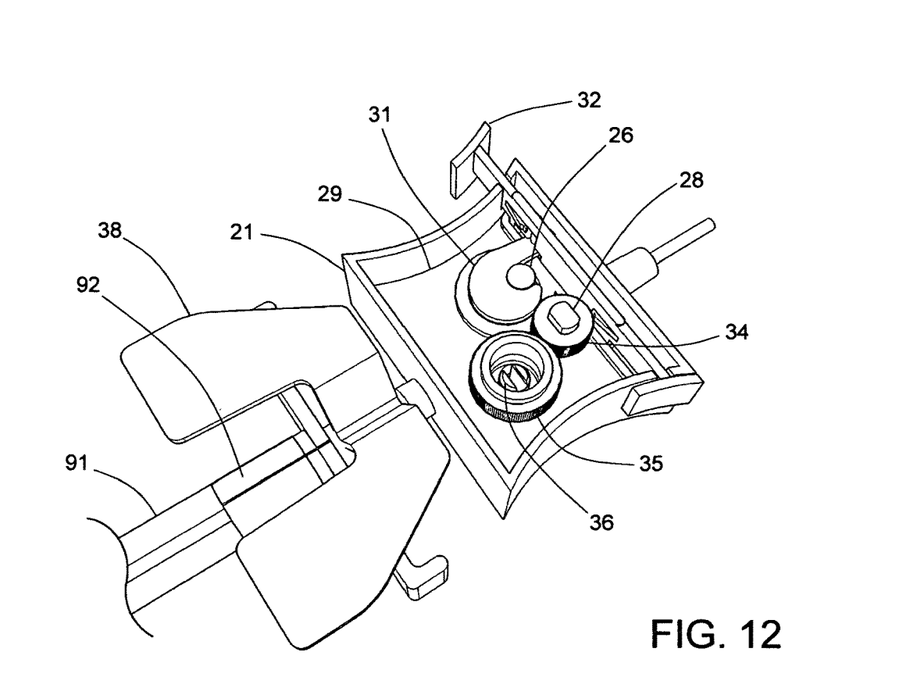
FIG. 12 is a perspective view of the housing from the bottom with the drive gears in the disengaged position.

FIG. 12 shows a perspective view from the bottom of the housing 21. The internal sealing cap 29 has been inserted and sealed to the housing 21. The movable drive rotating arm 31 pin is positioned within the external engagement actuator 32. When the external engagement actuator 32 is moved, the movable drive rotating arm 31 is rotated around the movable drive rotating arm 31 axis. Rotation of the movable drive rotating arm 31 causes the movable drive bottom 25 and the movable drive top 27 to rotate around the movable drive rotating arm 31 axis. The movable drive bottom 25 and the moveable drive top 27 rotation cause the moveable cylindrical catheter drive 26 axis and the fixed cylindrical catheter drive 28 axis spacing to change. The external engagement actuator 32 movement provides the external input for the catheter drive assembly 20 to engage or disengage with the flexible catheter 50. A fixed drive gear 34 is located on the fixed cylindrical catheter drive 28 shaft. The fixed drive gear 34 axis of rotation is the same as the fixed cylindrical catheter drive 28 axis of rotation. A main drive gear 35 position is maintained by the internal sealing cap 29. The fixed drive gear 34 and the main drive gear 35 axes spacing is fixed to maintain the fixed drive gear 34 and the main drive gear 35 in meshing engagement. An external drive 36 shaft is inserted through the housing 21 top surface. The external drive 36 locks into the main drive gear 35. The external drive 36 axis of rotation is the same as the main drive gear 35 axis of rotation. In the co-pending application a drive gear was also shown being located on the shaft of the movable cylindrical catheter drive 26. When in the engaged position, the drive gear on the movable cylindrical catheter drive 26 was in messing engagement with the fixed drive gear 34. In this arrangement both the movable cylindrical catheter drive 26 and the fix cylindrical catheter drive 28 had driven rotation in opposite directions. The following features are described in the co-pending application and form no part of the present invention. It may be desirable to have one of the cylindrical catheter drives as an idler. FIG. 12 shows the movable cylindrical catheter drive 26 as being the idler. The main drive gear 35 and the fixed drive gear 34 are in continuous messing engagement. The fixed cylindrical catheter drive 28 can also be arranged to be the idler. The movable cylindrical catheter drive 26 would have a drive gear mounted on the shaft. When in the engaged position the drive gear on the shaft of the movable cylindrical catheter drive 26 would be in messing engagement with the main drive gear 35. The fixed cylindrical catheter drive 28 would be the idler. Either cylindrical catheter drive has the capability of being the idler.

Figure 13:
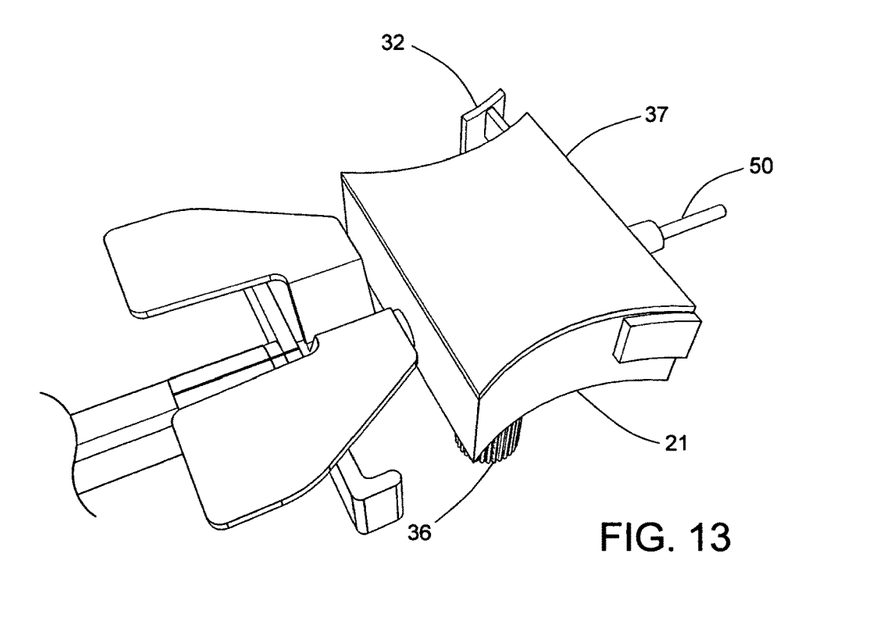
FIG. 13 is a perspective view of the housing from the bottom with the bottom cover installed.

FIG. 13 shows a perspective view from the bottom of the bottom cover 37. The bottom cover 37 is joined to the housing 21 completing the catheter drive assembly 20. The bottom cover 37 and the external engagement actuator 32 have interfacing features that maintain the catheter drive assembly 20 in the desired engaged or disengaged position. The following features are described in the co-pending application and form no part of the present invention. The materials used for the manufacture of the components of the catheter drive assembly 20 would preferably have the characteristics of acceptable medical grade plastic that can be precision molded and adapted to maintain its dimensions under normal hospital conditions. The housing 21 and removable cover 39 would be made from an acceptable clear medical grade plastic.

Figure 14:
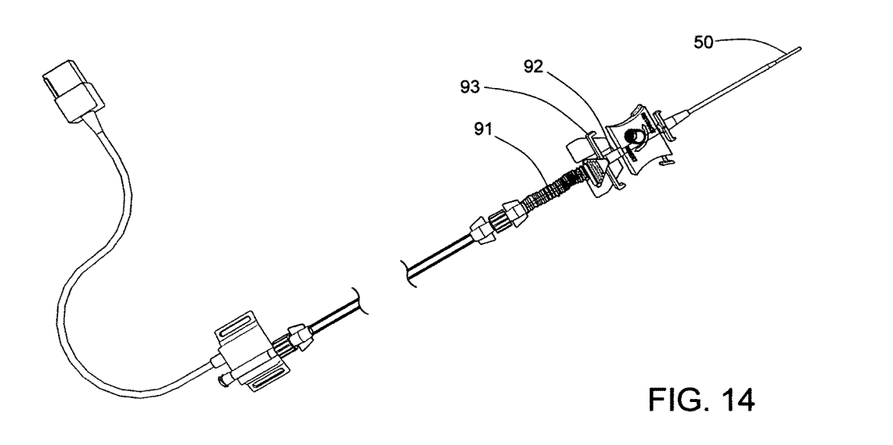
FIG. 14 is a perspective view of the device after a single lumen catheter has been inserted with the protective sleeve compressed.

FIG. 14 shows a perspective view of the catheter insertion assembly 100 showing the flexible catheter 50 after it has been inserted into the vessel to the desired position. When the flexible catheter 50 is inserted into the vessel the protective sleeve 91 is compressed. The perspective view shows the protective sleeve 91 fully compressed.

Figure 15:
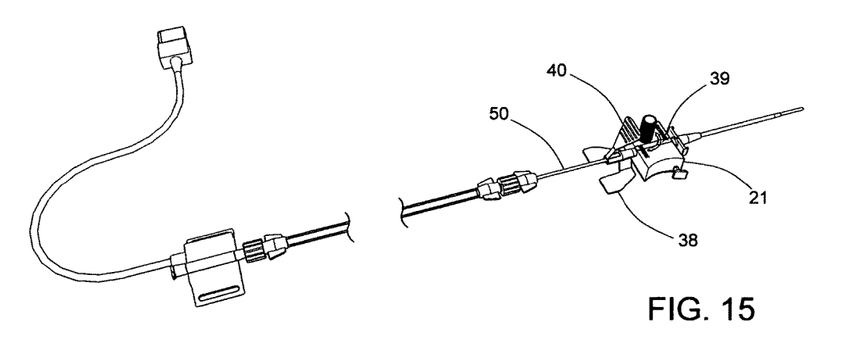
FIG. 15 is a perspective view of the device after the single lumen catheter has been inserted with the protective sleeve removed.

FIG. 15 is a perspective view of the catheter insertion assembly 100 after the flexible catheter 50 has been inserted into the vessel to the desired position. The protective sleeve assembly 90 has been separated and removed from the flexible catheter 50.

Figure 16:
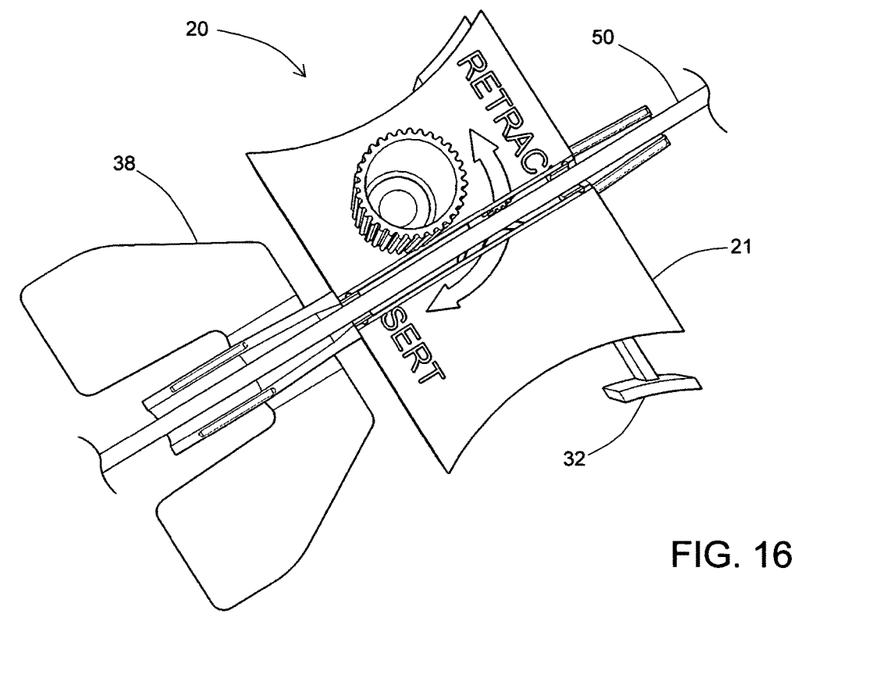
FIG. 16 is a perspective view of the catheter drive assembly with the removable cover removed showing the flexible catheter.

FIG. 16 is a perspective view of the catheter drive assembly 20 from the top. The removable cover 39 has been removed from the catheter drive assembly 20. With the removable cover 39 removed the flexible catheter 50 is exposed. Removal of the removable cover 39 provides full longitudinal access to the flexible catheter 50 within the catheter drive assembly 20. With the external engagement actuator 32 in the disengaged position, the flexible catheter 50 can be removed from the catheter drive assembly 20. A flexible catheter 50 with a single or multiple flexible catheter proximal end with connector(s) 52 can be removed from the catheter drive assembly 20. The movable drive bottom 25 has a flat section to allow the flexible catheter 50 to be removed from the top of the catheter drive assembly 20. In the engaged position, the movable drive bottom 25 blocks the flexible catheter 50 from being removed from the top of the catheter drive assembly 20. This feature prohibits the attempt to remove the flexible catheter 50 from the catheter drive assembly 20 while in the engaged position and possibly damaging the flexible catheter 50. After removal, the catheter drive assembly 20 can be disposed of while leaving the flexible catheter 50 inserted into the vessel.

Operation of the Embodiment

Prior to use of the catheter insertion assembly 100, the distance from the desired placement of the flexible catheter distal end 51 to the desired catheter insertion site on the patient is measured. The measurement determines the length of the flexible catheter 50 to be inserted into the patient.

Referring to FIG. 1, the end shield 41 is removed from the catheter drive assembly 20 exposing the flexible catheter distal end 51. If the blood pressure is to be monitored during insertion then prior to insertion of the flexible catheter 50 into a patient the user primes the catheter insertion assembly 100. The disposable blood pressure transducer proximal connector 72 is attached to an intravenous solution source (not shown) in a conventional manner as is well known in the relevant technology. The user introduces the priming fluid into the catheter insertion assembly 100. The user holds the catheter insertion assembly 100 by the catheter drive assembly 20 thereby positioning the catheter insertion assembly 100 in a vertical position with the flexible catheter distal end 51 upward. Fluid flows through and fills the disposable blood pressure transducer 70. Fluid flow through and fills the pressure line 60. Fluid flows into the flexible catheter 50 at the flexible catheter proximal end with connector 52. When fluid is observed being expressed out of the flexible catheter distal end 51 the catheter insertion assembly 100 is primed.

After the catheter insertion assembly 100 is primed the user may proceed to insert the flexible catheter 50 into the patient. The introducer sheath 80 would already be in place within the patient's vein in a conventional manner as is well known in the relevant technology. The user pushes the external engagement actuator 32 on the catheter drive assembly 20 to the engaged position. Holding the catheter drive assembly 20, the user inserts the flexible catheter distal end 51 into introducer sheath proximal connector 81. The user pushes the catheter drive assembly 20 forward until the housing distal connector 22 connects with the introducer sheath proximal connector 81. The disposable blood pressure transducer plug connector 74 is connected to a blood pressure monitor (not shown).

The user, with one hand, holds the catheter drive assembly 20 between their fingers. The user, with their other hand, rotates the external drive 36 with their fingers. The external drive 36 is rotated in the desired direction to advance or retract the flexible catheter 50. The user advances the flexible catheter 50 a short distance, stops and observers the pressure reading on the blood pressure monitor. The protective sleeve 91, and the removable cover 39 are made of a clear material. During insertion the user visually monitors the movement and the inserted length of the flexible catheter 50. During insertion the flexible catheter 50 moves with the flow of blood in the vein. Assuming that the desired placement of the flexible catheter distal end 51 is the superior vena cava, the flexible catheter 50 can go in the wrong direction and go into the internal jugular vein and be directed toward cerebral circulation. If this was to occur, the flexible catheter 50 movement would change from moving with the flow of blood to moving against the flow of blood. The flexible catheter 50 moving against the flow of blood causes the pressure to increase and this increase would be displayed on the blood pressure monitor. The user rotates the external drive 36 in the opposite direction to retract the flexible catheter 50. The flexible catheter 50 is retracted until a lower blood pressure consistent with prior observations is achieved. The user rotates the external drive 36 to advance the flexible catheter 50. When the flexible catheter distal end 51 reaches the superior vena cava the central venous pressure waveform will be displayed on the blood pressure monitor. The user confirms the length of the flexible catheter 50 inserted into the patient. The central venous pressure waveform and the inserted length of the flexible catheter 50 confirms placement of the flexible catheter distal end 51. As the flexible catheter 50 is inserted into the vessel the protective sleeve 91 is compressed. The flexible catheter 50 remains encapsulated by the catheter drive assembly 20 and the protective sleeve assembly 90 during the insertion and retraction. The outside diameter of the flexible catheter 50 is only slightly smaller than the inside diameter of the introducer sheath tubular member 82 thereby minimizing blood leakage into the catheter drive assembly 20.

To remove the catheter drive assembly 20, the user grasps the two sleeve pull tabs 93 on the protective sleeve collar 92 and pulls thereby separating the protective sleeve collar 92. The user continues to pull the two halves of the protective sleeve collar 92 apart. The protective sleeve 91 is attached to the protective sleeve collar 92. As the user continues to pull the protective sleeve collar 92 apart, the protective sleeve 91 is separated thus removing it from the flexible catheter 50. Once the protective sleeve assembly 90 is removed from the flexible catheter 50 it can be discarded. The user moves the external engagement actuator 32 to the disengaged position. The user squeezes and holds the introducer sheath tubular member 82 just below the introducer sheath proximal connector 81 holding the flexible catheter 50 in position. The user then pulls the catheter drive assembly 20 away from the introducer sheath 80 disconnecting the housing distal connector 22 from the introducer sheath proximal connector 81. The catheter drive assembly 20 continues to be pulled away until the housing distal connector 22 is clear of the introducer sheath proximal connector 81. The catheter drive assembly 20 is continued to be pulled away from the introducer sheath 80 until approximately 1 inch of flexible catheter 50 is visible between the housing distal connector 22 and the introducer sheath proximal connector 81. The user uses two fingers to press down on the housing finger flange 38 to hold the housing 21 against the patient. With the other hand, the user grasps the cover pullout tab 40 and pulls away from housing 21 to remove the removable cover 39. Through the opening that is created in the housing 21 by removal of the removable cover 39, the flexible catheter 50 is lifted out of the catheter drive assembly 20. The catheter drive assembly 20 is discarded. Holding the flexible catheter 50 in position, the introducer sheath 80 is removed from the vein and separated from the flexible catheter 50 using standard clinical practice. If a multi lumen catheter having a wire or a stylet was used, the wire or stylet is removed. Using standard clinical procedure, the area around the catheter site is cleaned and secured. Any additional lumens in the flexible catheter 50 are aspirated prior to use using standard clinical practice.

Another aspect of the invention is a method to insert a flexible catheter 50 into a patient that does not require the monitoring of blood pressure during the insertion. In this setting, a specified length of flexible catheter 50 is inserted into the patient's vein. In this embodiment, the pressure line 60 and the disposable blood pressure transducer 70 that is shown in FIG. 1 are eliminated as components of the catheter insertion assembly 100. The introducer sheath 80 would already be in place within the patient's vein in a conventional manner as is well known in the relevant technology. The user pushes the external engagement actuator 32 on the catheter drive assembly 20 to the engaged position. Holding the catheter drive assembly 20, the user inserts the flexible catheter distal end 51 into introducer sheath proximal connector 81. The user pushes the catheter drive assembly 20 forward until the housing distal connector 22 connects with the introducer sheath proximal connector 81. The user, with one hand, holds the catheter drive assembly 20 between their fingers. The user, with their other hand, rotates the external drive 36 with their fingers. The external drive 36 is rotated in the desired direction to advance the flexible catheter 50. The protective sleeve 91 and the removable cover 39 are made of a clear material. The user can visually monitor the movement and the inserted length of the flexible catheter 50. The user advances the flexible catheter 50 until the desired length of the flexible catheter 50 is inserted into the vein. As the flexible catheter 50 is inserted into the vessel the protective sleeve 91 is compressed. The flexible catheter 50 remains encapsulated by the catheter drive assembly 20 and the protective sleeve 91 during the insertion. The outside diameter of the flexible catheter 50 is only slightly smaller than the insider diameter of the introducer sheath tubular member 82 thereby minimizing blood leakage into the catheter drive assembly 20.

To remove the catheter drive assembly 20, the user grasps the sleeve pull tabs 93 on the protective sleeve collar 92 and pulls thereby separating the protective sleeve collar 92. The user continues to pull the two halves of the protective sleeve collar 92 apart. The protective sleeve 91 is attached to the protective sleeve collar 92. As the user pulls the protective sleeve collar 92 halves apart, the protective sleeve 91 is separated thereby removing it from the flexible catheter 50. Once the protective sleeve assembly 90 is removed from the flexible catheter 50, it is discarded. The user moves the external engagement actuator 32 to the disengaged position. The user squeezes and holds the introducer sheath tubular member 82 just below the introducer sheath proximal connector 81 holding the flexible catheter 50 in position. The user then pulls the catheter drive assembly 20 away from the introducer sheath 80 disconnecting the housing distal connector 22 from the introducer sheath proximal connector 81. The catheter drive assembly 20 continues to be pulled away until the housing distal connector 22 is clear of the introducer sheath proximal connector 81. The catheter drive assembly 20 is continued to be pulled away from the introducer sheath 80 until approximately 1 inch of flexible catheter 50 is visible between the housing distal connector 22 and the introducer sheath proximal connector 81. The user uses two fingers to press down on the housing finger flange 38 to hold the housing 21 against the patient. With the other hand, the user grasps the cover pullout tab 40 and pulls away from housing 21 thereby removing the removable cover 39. Through the opening that was created in the housing 21 by removal of the removable cover 39, the flexible catheter 50 is lifted out of the catheter drive assembly 20. The catheter drive assembly 20 is discarded. Holding the flexible catheter 50 in position, the introducer sheath 80 is removed from the vein and separated from the flexible catheter 50 using standard clinical practice. If a multi lumen catheter having a wire or a stylet was used, the wire or stylet is removed. Using standard clinical procedure, the area around the catheter site is cleaned and secured. All lumens in the flexible catheter 50 are aspirated prior to use using standard clinical practice.

Advantages

From the description above, a number of advantages of the embodiments of my method and apparatus for catheter insertion while monitoring blood pressure become evident:
(a) The flexible catheter 50 is completely encapsulated thereby creating a closed system needed for aseptic insertion of the flexible catheter.
(b) The catheter insertion assembly 100 can be primed with the appropriate solution minimizing the risk of an air embolism.
(c) The flexible catheter 50 is completely encapsulated eliminating the need for a maximal sterile barrier.
(d) The flexible catheter 50 can be advanced into the patient and retracted from the patient while remaining in an encapsulated sterile environment.
(e) The flexible catheter 50 can be advanced into the patient and retracted from the patient with equal ease.
(f) The versatility to advance and retract can be readily employed to manipulate the advancing flexible catheter distal end 51 past obstructions.
(g) The flexible catheter 50 can be inserted in a few minutes by eliminating the time needed to establish a maximal sterile barrier.
(h) The apparatus provides the capability to monitor blood pressure readings during the insertion process.
(i) The apparatus can verify the flexible catheter distal end 51 placement by observing the central venous pressure waveform and the inserted length of flexible catheter 50 thus eliminating the need for Ultra Sound or X-ray verification.
(j) The apparatus can insert the flexible catheter 50 in an emergency or combat setting because the apparatus is a closed system.
(k) The apparatus can be sterilized and stored for an extended period of time prior to use without deforming the flexible catheter 50.
(l) The apparatus can be used with conventional catheters that have a pre-attached connector on the proximal end.
(m) The apparatus can be used with catheters that have multi lumens and with or without a wire or stylet.

Although the description above contains many specificities, these should not be construed as limiting the scope of the embodiment but as merely providing illustrations of the embodiment. Many other ramifications and variations are possible within the teachings of the embodiment.

Thus the scope should be determined by the appended claims and their legal equivalents, and not by the examples given.

I claim:
1. In a catheter insertion assembly comprising: a disposable blood pressure transducer, a pressure tubing, a catheter drive assembly comprising a housing and a catheter drive mechanism disposed therein, a flexible catheter, an introducer sheath, an intravenous solution source, the improvements comprising:
a) said catheter drive assembly comprising: a housing and a catheter drive mechanism disposed therein, comprising:
i) a fixed cylindrical catheter drive comprising a fixed drive gear; and an opposing movable cylindrical catheter drive comprising a movable drive bottom, a movable drive top and a movable drive gear mounted therebetween, said movable cylindrical catheter drive configured to be moved between an engaged and a disengaged relationship with said fixed cylindrical catheter drive so as to selectively grip said flexible catheter inserted therebetween when in said engaged relationship so as to move said inserted flexible catheter;
ii) an external drive coaxially connected to a main drive gear, said main drive gear being disposed in fixed engagement with said fixed drive gear;
iii) an external engagement actuator movable between an engaged and a disengaged position, said external engagement actuator being operatively connected to a movable drive rotating arm disposed above and affixed to said movable drive top such that movement of said external engagement actuator between said engaged position and said disengaged position moves said movable cylindrical catheter drive between said engaged relationship and said disengaged relationship; and
iv) said housing comprising a housing distal connector disposed on a forward-facing side of said housing, a housing proximal connector disposed on an opposing rearward-facing side of said housing, a bottom cover comprising an internal seal, and a removable top cover disposed along a length of said housing from the said housing distal connector to said housing proximal connector creating an opening for selective removal of said flexible catheter;
b) said catheter drive assembly further comprising an end shield engaged to said housing distal connector.

2. The improved catheter insertion assembly as recited in claim 1, wherein said flexible catheter inserted into said catheter insertion assembly comprises a protective sleeve assembly enclosing said flexible catheter, said protective sleeve assembly comprising a distal end that engages said housing proximal connector, said protective sleeve assembly extending from said housing proximal connector to said flexible catheter proximal end connector.

3. The catheter insertion assembly of claim 2 wherein said protective sleeve assembly comprises a protective sleeve and a protective sleeve collar, said protective sleeve being attached to said protective sleeve collar, said protective sleeve collar comprising a pair of pull tabs integral with said protective sleeve collar and extending laterally outwardly there from, said protective sleeve collar being disposed in a tubular portion having opposed weakened portions, said pull tabs of said protective sleeve collar when pulled apart facilitate tearing of said protective sleeve assembly axially from said flexible catheter.

4. The catheter insertion assembly of claim 2 wherein said protective sleeve assembly comprises a protective sleeve and a protective sleeve collar, said protective sleeve being attached to said protective sleeve collar, said protective sleeve collar comprising a pair of pull tabs integral with said protective sleeve collar and extending laterally outwardly there from, said protective sleeve collar being disposed in a tubular portion having opposed weakened portions, said pull tabs of said protective sleeve collar when pulled apart facilitate tearing of said protective sleeve assembly axially from said flexible catheter.

5. The catheter insertion assembly of claim 1 wherein said flexible catheter inserted in said catheter insertion assembly is selected from the group consisting of: a single lumen catheter, a multi lumen catheter, a wire, and a stylet.

6. The catheter insertion assembly of claim 1 wherein said housing forms a portion of said housing distal connector and said housing proximal connector, said removable cover forms a portion of said housing distal connector and said housing proximal connector, when said housing and said removable cover are joined said housing distal connector is formed and said housing proximal connector is formed, said housing having a flange, said flange supporting said housing during the removal of said removable cover.

7. The improved catheter insertion assembly as recited in claim 1, wherein one of said fixed cylindrical catheter drive and said movable cylindrical catheter drive functions as an idler.

8. The improved catheter insertion assembly as recited in claim 1, wherein said flexible catheter inserted into said catheter insertion assembly comprises a connector pre-attached to a proximal end of said flexible catheter configured for attachment to a distal connector of said pressure tubing.

9. In a catheter insertion assembly comprising: a catheter drive assembly comprising a housing, a catheter drive mechanism, a flexible catheter, and an introducer sheath, the improvements comprising:
   a) said housing comprising a housing distal connector disposed on a forward-facing side of said housing, a housing proximal connector disposed on an opposing rearward-facing side of said housing, and a removable top cover disposed along a length of said housing from the said housing distal connector to said housing proximal connector creating an opening for selective removal of said flexible catheter; and
   b) said catheter drive assembly comprising: a fixed cylindrical catheter drive comprising a fixed drive gear, and a movable cylindrical catheter drive comprising a movable drive bottom, a movable drive top and a movable drive gear mounted therebetween, said movable drive bottom configured to prevent removal of said flexible catheter from said catheter drive assembly when said catheter drive mechanism is engaged, said catheter drive assembly having an end shield engaged to said housing distal connector.

10. The improved catheter insertion assembly as recited in claim 9, wherein said flexible catheter inserted into said catheter insertion assembly comprises a connector pre-attached to a proximal end of said flexible catheter configured for attachment to a distal connector of said pressure tubing.

11. The improved catheter insertion assembly as recited in claim 10, wherein said flexible catheter inserted into said catheter insertion comprises a protective sleeve assembly enclosing said flexible catheter, said protective sleeve assembly comprising a distal end that engages said housing proximal connector, said protective sleeve assembly extending from said housing proximal connector to said flexible catheter proximal end connector.

12. The catheter insertion assembly of claim 9 wherein said flexible catheter inserted in said catheter insertion assembly is selected from the group consisting of: a single lumen catheter, a multi lumen catheter, a wire, and a stylet.

13. The catheter insertion assembly of claim 9 wherein said housing forms a portion of said housing distal connector and said housing proximal connector, said removable cover forms a portion of said housing distal connector and said housing proximal connector, whereas when said housing and said removable cover are joined said housing distal connector is formed and said housing proximal connector is formed, said housing having a flange, said flange supporting said housing during the removal of said removable cover.

14. The improved catheter insertion assembly as recited in claim 9, wherein one of said fixed cylindrical catheter drive and said movable cylindrical catheter drive functions as an idler.

* * * * *